United States Patent
Koo et al.

(10) Patent No.: US 10,760,082 B2
(45) Date of Patent: Sep. 1, 2020

(54) CANCER-TREATING PHARMACEUTICAL COMPOSITION INHIBITING EXPRESSION OF CCND3 OR PAK2 GENE

(71) Applicant: KOREA INSTITUTE OF RADIOLOGICAL & MEDICAL SCIENCES, Seoul (KR)

(72) Inventors: Kyung Hee Koo, Seoul (KR); Hee Chung Kwon, Namyangju-si (KR); Jie Young Song, Seoul (KR)

(73) Assignee: Korea Institute of Radiological & Medical Sciences, Seoul (KR)

( * ) Notice: Subject to any disclaimer, the term of this patent is extended or adjusted under 35 U.S.C. 154(b) by 0 days.

(21) Appl. No.: 16/346,078

(22) PCT Filed: Dec. 21, 2017

(86) PCT No.: PCT/KR2017/015260
§ 371 (c)(1),
(2) Date: Apr. 29, 2019

(87) PCT Pub. No.: WO2018/124640
PCT Pub. Date: Jul. 5, 2018

(65) Prior Publication Data
US 2019/0256857 A1    Aug. 22, 2019

(30) Foreign Application Priority Data
Dec. 26, 2016  (KR) ......................... 10-2016-0179127

(51) Int. Cl.
| | | |
|---|---|---|
| *A61K 48/00* | (2006.01) | |
| *C07H 21/04* | (2006.01) | |
| *C12N 15/113* | (2010.01) | |
| *A61P 35/00* | (2006.01) | |
| *G01N 33/68* | (2006.01) | |
| *C12Q 1/68* | (2018.01) | |

(52) U.S. Cl.
CPC .......... *C12N 15/1137* (2013.01); *A61K 48/00* (2013.01); *A61P 35/00* (2018.01); *C12N 15/113* (2013.01); *C12Q 1/68* (2013.01); *G01N 33/68* (2013.01); *C12N 2310/141* (2013.01); *C12Y 207/11001* (2013.01)

(58) Field of Classification Search
CPC ............................ A61K 31/713; C12N 15/113
See application file for complete search history.

(56) References Cited

U.S. PATENT DOCUMENTS

2018/0030440 A1    2/2018  Lee et al.

FOREIGN PATENT DOCUMENTS

| KR | 10-2015-0003111 | 1/2015 |
| KR | 10-2015-0123213 | 11/2015 |
| KR | 10-2016-0103949 | 9/2016 |

OTHER PUBLICATIONS

Liu et al. (Int J Clin Exp Med 2015;8(3):3490-3497).*
Gou et al. (Physiol Genomics, 31, 554-562, 2007).*
Hao et al., "miR-137 inhibits proliferation of melanoma cells by targeting PAK2," *Experimental Dermatology*, vol. 24, pp. 947-952, 2015.
International Search Report for PCT/KR2017/015260, dated Mar. 27, 2018 (3 pages, English translation).
Liu et al., "MiR-592 inhibited call proliferation of human colorectal cancer cells by suppressing of CCND3 expression," *Int. J. Clin. Exp. Med.*, vol. 8, No. 3, pp. 3490-3497, 2015.
Office Action issued in KR App. No. 10-2016-179127, dated Mar. 4, 2018 (7 pages).
Office Action issued in KR App. No. 10-2016-179127, dated Nov. 6, 2018 (4 pages).

* cited by examiner

*Primary Examiner* — Amy H Bowman
(74) *Attorney, Agent, or Firm* — Klarquist Sparkman, LLP (57) ABSTRACT

A substance inhibiting the expression of CCND3 gene or PAK2 gene, the substance containing a nucleotide such as miR-4779, may be efficiently used for preventing or treating cancer. In addition, by screening the substance that inhibits the expression of CCND3 gene or PAK2 gene, a candidate substance for preventing or treating cancer may be selected.

8 Claims, 9 Drawing Sheets

Specification includes a Sequence Listing.

FIG. 1A. MTS assay

FIG. 1B. Cell morphology

FIG. 1D. Apoptosis

FIG. 1C. Cell cycle

FIG. 2A. Colony forming assay

FIG. 2B. Soft agar assay

FIG. 3A. MTS assay

FIG. 3B. Cell morphology

FIG. 3C. Cell cycle

FIG. 4A. colony forming assay

FIG. 4B. Soft agar assay

FIG. 5A. qPCR

FIG. 7A. qPCR

FIG. 7B. MTS assay

FIG. 7C. Cell morphology

FIG. 8A. Cell cycle

FIG. 8B. Apoptosis assay

FIG. 8C. Colony forming assay

FIG. 8D. Soft agar assay

CANCER-TREATING PHARMACEUTICAL COMPOSITION INHIBITING EXPRESSION OF CCND3 OR PAK2 GENE

CROSS REFERENCE TO RELATED APPLICATIONS

This is the U.S. National Stage of International Application No. PCT/KR2017/015260, filed Dec. 21, 2017, which claims the benefit of KR Application No. 10-2016-0179127, filed Dec. 26, 2016, which is incorporated herein by reference in its entirety.

TECHNICAL FIELD

The present disclosure relates to a cancer-treating pharmaceutical composition that inhibits the expression of CCND3 gene or PAK2 gene.

BACKGROUND ART

Methods for treating cancer are largely classified into surgical treatment, chemotherapy, and radiation therapy. In general, these treatments and therapies are used in combination depending on the type and progression of the cancer. These diverse and complex chemotherapeutic treatments work on not only cancer cells, but also normal cells, causing several side effects. In addition, there is a problem that the treatment efficiency may be reduced by obtaining the resistance of cancer cells to anticancer agents or the radiation resistance. Therefore, there is an urgent demand for the development of radiation sensitive enhancers and anticancer agents capable of minimizing side effects while enhancing effects of chemotherapy.

Meanwhile, several miRNAs are specifically expression during tumor formation and metastasis, and have been found to act as tumor genes or tumor inhibitor when the expression of each of a variety of target genes is controlled. In addition, the expression pattern of specific miRNAs between normal tissues and cancer tissues has increased the possibility of miRNAs as predictive markers in the treatment of cancer. To date, it has been reported that 2588 mature miRNAs are found in humans (miRBase release 21), but many miRNA functions are not yet known. Therefore, targeting new human miRNA libraries that continue to discover, there is a growing need for research to identify and characterize candidate miRNAs that are more efficacious for enhancing anticancer and radiation sensitivity.

DESCRIPTION OF EMBODIMENTS

Technical Problem

Provided is a pharmaceutical composition for preventing or treating cancer, pharmaceutical composition including, as an active ingredient, a substance inhibiting the expression of cyclin D3 (CCND3) gene or p21-activated kinase 2 (PAK2) gene.

Provided is a pharmaceutical composition for preventing or treating cancer, the pharmaceutical composition including, as an active ingredient, an agent inducing generation of miRNA inhibiting the expression of CCND3 gene or PAK2 gene.

Provided is a nucleotide for preventing or treating cancer, the nucleotide inhibiting the expression of CCND3 gene or PAK2 gene.

Provided is a method of screening a candidate substance for preventing or treating cancer, the candidate substance inhibiting the expression of CCND3 gene or PAK2 gene.

Solution to Problem

An aspect of the present disclosure provides a pharmaceutical composition for preventing or treating cancer, the pharmaceutical composition including, as an active ingredient, a substance inhibiting the expression of cyclin D3 (CCND3) gene or p21-activated kinase 2 (PAK2 gene).

"Cyclin D3 (CCND3)" is one of cyclin genes that function as regulators of CDK kinases. In particular, the CCND3 cyclin is known to play an important function at the G1/S transition stage of the cell cycle. The term "CCND3" as used herein should be understood to include CCND3 genes, mRNAs, proteins, or fragments thereof.

"PAK2 (p21-activated kinase 2)" is known as a gene being activated by proteolytic cleavage during caspase-mediated apoptosis and playing a major role in apoptosis. The protein expressed by this gene belongs to a family of serine/threonine kinases that serve as targets for the small GTP-binding proteins, such as CDC42 and RAC1. The term "PAK2" as used herein should be understood to include all the PAK2 genes, mRNAs, proteins, or fragments thereof.

The term "active ingredient" as used herein refers to an ingredient included in an amount sufficient to treat a disease at a reasonable benefit or risk ratio applicable to medical treatment, and can be used interchangeable with the expression "pharmaceutically effective amount". The effective amount may depend on factors including types of disease of an individual, severity, activity of drugs, sensitivity to drugs, time of administration, route of administration, rate of release, duration of treatment, and drugs being concurrently used, and other factors well known in the medical fields.

The cancer may include lung cancer, liver cancer, stomach cancer, colorectal cancer, colon cancer, pancreatic cancer, skin cancer, bladder cancer, prostate cancer, breast cancer, ovarian cancer, cervical cancer, thyroid cancer, renal cancer, fibrosarcoma, melanoma, and blood cancer. The cancer may also include cancer in a condition that is resistant to chemotherapy and radiation therapy.

The substance inhibiting the expression of CCND3 gene or PAK2 gene may include a primer, a probe, a nucleotide, an antibody or an antigen-binding fragment thereof, a ligand, a receptor, an agonist or an antagonist, a peptide, a polypeptide, a protein, or a combination thereof, wherein each of the foregoing specifically binds to mRNA or protein of CCND3 gene or PAK2 gene. The substance specifically binding to mRNA or protein of CCND3 gene or PAK2 gene may be selected from according to methods known in the art, such as a high throughput screening (HTS) method, and may be also commercially available.

The substance may be a consecutive nucleotide having a sequence complementarily binding to an mRNA sequence of CCND3 or PAK2, or 3'UTR of the mRNA sequence. The nucleotide may have a sequence having 60%, 70%, 80%, 90%, 95% or higher or 100% sequence identity with some or all of the mRNA sequence of CCND3 or PAK2. The nucleotide may be a consecutive nucleotide complementarily binding to at least one region of the mRNA sequence of CCND3 or PAK2. The nucleotide may be a consecutive nucleotide having a sequence complementarily binding to all of the mRNA sequence of CCND3 and PAK2.

The nucleotide may include 7 to 100 consecutive nucleotides, 7 to 30 consecutive nucleotides, 10 to 30 consecutive nucleotides, or 15 to 25 consecutive nucleotides, each of which consecutive nucleotides has a sequence complimentarily binding to a sequence of SEQ ID NO: 1. The nucleotide may include 7 to 100 consecutive nucleotides, 7 to 30 consecutive nucleotides, 10 to 30 consecutive nucleotides, or 15 to 25 consecutive nucleotides, each of which consecutive nucleotides has a sequence complimentarily binding to a sequence of SEQ ID NO: 2 The nucleotide may include 22 to 100 consecutive nucleotides, 22 to 30 consecutive nucleotides, or 22 to 25 consecutive nucleotides, each of which consecutive nucleotides has a sequence of SEQ ID NO: 3.

The nucleotide may be miRNA.

The term "miRNA" as used herein may be also referred to as microRNA or miR. The miRNA may be an RNA strand including about 10 to about 30 or about 21 to about 25 nucleotides in length. The miRNA is transcribed from DNA, but is not translated into protein, and thus is encoded by a gene including a non-coding RNA. The miR is processed into a short stem-loop structure, which is called pre-miRNA, from the known primary transcript pri-miRNA, and then is processed into a finally produced single-stranded mRNA. The pre-miRNA may form a self-infolding structure within a self-complementary region. The structure is then processed by a nuclease in the animal. A mature miRNA molecule may be partially complementary to at least one mRNA molecule, and may function to regulate transcription of protein. The miRNA is generally assigned a number according to the nomenclature as to "mir-[number]". The number of miRNA is assigned according to the sequence found for miRNA species that have been already identified. When the miRNA is found to be similar to the known miRNA of a different organism, its name is provided in the form of [organism identifier]-mir-[number], wherein the organism identifier is optionally provided. A mature microRNA is usually prefixed with "miR", and a gene or precursor miRNA is usually prefixed with "mir". In the description of the present specification, any microRNA prefixed with mir-* or miR-* (e.g., miRNA or miR) should be understood to include both precursors and/or mature species, unless explicitly stated otherwise.

The miRNA may be miRNA having a seed sequence complementarily binding to an mRNA sequence of CCND3 or PAK2 mRNA, or 3'UTR of the mRNA sequence. The miRNA may include miR-4779.

The pharmaceutical composition may be used as an independent anticancer agent or in combination with other anticancer agents, or may be used in combination with other chemotherapeutic treatments, such as surgical treatment, surgical treatment, chemotherapy, or radiation therapy. The pharmaceutical composition may increase the efficiency of radiation therapy by enhancing the radiation sensitivity of cancer cells.

The present inventors confirmed that miR-4779 inhibits the expression of CCND3 and PAK2, and accordingly, also confirmed that the cell viability of cancer cells is lowered while the radiation sensitivity of cancer cells is increased. Therefore, the substance including miR-4779 and inhibiting the expression of CCND3 gene or PAK2 gene may be applicable for the prevention or treatment of cancer.

Another aspect of the present disclosure provides a pharmaceutical composition for preventing or treating cancer, the pharmaceutical composition including, as an active ingredient, an agent inducing generation of miRNA and inhibiting the expression of CCND3 gene or PAK2 gene.

The agent inducing the generation of miRNA may include an miRNA expression vector.

The term "vector" as used herein refers to a means for expressing a desired gene in a host cell, and also refers to a nucleotide which is independently replicated and produces a copy of a vector or a foreign DNA inserted in the vector when introduced into a host cell. The term "recombinant expression vector" or "expression vector" as used herein refers to a vector to which a foreign DNA fragment is inserted for the purpose of amplification of a specific protein, wherein the foreign DNA fragment may be a polynucleotide encoding a specific polypeptide or RNA. The establishment of a vector system for the expression or cloning purposes may be carried out according to the conventional methods known in the art. The vector may include a regulatory sequence linked to a sequence of the polynucleotide defined herein. The term "regulatory sequence" as used herein refers to a nucleotide acid sequence necessary to enable the expression of a coding sequence, and the nature of the regulatory sequence may vary depending on a host organism. The expression vector may further include, in addition to the regulatory sequence, a restriction enzyme cleavage site, a marker gene such as a drug-resistant gene, a secretory signal sequence, or a leader sequence. The restriction enzyme cleavage site refers to a specific base sequence that is specifically recognized and cleaved by a restriction enzyme. The cleavage site may include, for example, a sequence that is specifically recognized by a restriction enzyme, such as EcoRI, BamHI, HindIII, kpn I, SalI, Not I, Pst I, Sma I, and Xho I. The marker gene may serve as a selectable marker, and may be a resistance gene of drugs such as ampicillin, genamycin, carbenicillin, chloramphenicol, streptomycin, kanamycin, geneticin, neomycin, and tetracycline. The secretory signal sequence or the leader sequence refers to a sequence that directs a synthesized protein toward a cell compartment (for example, a periplasmic space) or a sequence that induces secretion into an extracellular medium, and may be added to a coding sequence of the above-mentioned polynucleotide sequence. Such sequences above may be appropriately selected from by one of ordinary skill in the art depending on DNA to be introduced, types of a host cell, and conditions of a culture medium.

The above-mentioned terms or elements among terms and elements used herein are defined the same as above.

Another aspect of the present disclosure provides a nucleotide for preventing or treating cancer, the nucleotide inhibiting the expression of CCND3 gene or PAK2 gene. The nucleotide is the same as described above.

Another aspect of the present disclosure provides a method of screening a candidate substance for preventing or treating cancer, the candidate substance inhibiting the expression of CCND3 gene or PAK2 gene.

The method may include: contacting a substance to be tested with a cell expressing cyclin D3 (CCND3) gene or p21-activated kinase 2 (PAK2) gene; measuring the expression level of the CCND3 gene or PAK2 gene in the cell being in contact with the substance to be tested; and screening the substance to be tested which changes the gene expression level.

In one or more embodiments, the method may include: contacting a substance to be tested with a sample containing mRNAs or proteins of CCND3 or PAK2, or fragments of the mRNAs or the proteins; measuring a binding level of the substance to be tested to the mRNAs or the proteins, or the fragments of the mRNAs or the proteins, in the sample being in contact with the substance to be tested; contacting the substance to be tested with a sample containing a nucleotide which has some or all of the mRNA sequence of CCND3 or PAK2; measuring a binding level of the substance to be tested to the nucleotide in the sample being in contact with the substance to be tested; and screening the substance to be tested which specifically binds to the nucleotide.

The candidate substance may be any natural or synthesized substance which is expected to efficiently prevent or treat cancer by inhibiting the expression of CCND3 or PAK2. The cell may be separated from a part of an individual or from an individual.

The measuring may be performed by detecting a signal from a detectable label attached to a substance that specifically binds to mRNAs or proteins of CCND3 or PAK2. In one or more embodiments, the measuring may be performed by detecting a signal from a detectable label attached to a substance that specifically binds to the substance to be tested. The measuring may be performed according to protocols known in the art using RT-PCR, competitive RT-PCR, real-time RT-PCR, RNase protection assay (RPA), northern blotting, nucleic acid microarray including DNA, western blotting, enzyme linked immunosorbent assay (ELISA), radioimmunoassay (RIA), radioimmunodiffusion, Ouchterlony immunodiffusion, rocket immunoelectrophoresis, immunohistochemical staining, immunoprecipitation assay, complement fixation assay, FACS, mass spectrometry, magnetic bead-antibody immunoprecipitation, protein chip, or a combination thereof.

The method may include determining the substance to be tested as a candidate substance that may be effective in the cancer treatment, when the expression level of CCND3 gene or PAK2 gene in the cell is changed in comparison with the expression level in a control group. The change in the expression level may include, in comparison with the expression level in the control group, an increase in the expression level of the individual by 1%, 2%, 3%, 4%, 5%, 10%, 20%, 30%, 40%, 50%, 60%, 70%, 80%, 90%, 100%, 200%, 300%, 400%, 500%, 600%, 700%, 800%, 900%, and 1,000% or more, or a decrease in the expression level of the individual by 1%, 2%, 3%, 4%, 5%, 10%, 20%, 30%, 40%, 50%, 60%, 70%, 80%, 90%, and 100% or more.

The method may also include determining the substance to be tested as a candidate substance that may be effective in the cancer treatment, when the substance to be tested specifically binds to mRNAs or proteins of the CCND3 gene or the PAK2 gene, or fragments of the mRNAs or the proteins.

Advantageous Effects of Disclosure

According to an aspect of the present disclosure, a substance inhibiting the expression of CCND3 gene or PAK2 gene may be efficiently used to prevent or treat cancer.

According to another aspect of the present disclosure, a cancer pharmaceutical composition for preventing or treating cancer, the pharmaceutical composition including, as an active ingredient, an agent inducing generation of miRNA and inhibiting the expression of CCND3 gene or PAK2 gene may efficiently prevent or treat cancer.

According to another aspect of the present disclosure, a nucleotide inhibiting the expression of CCND3 gene or PAK2 gene may be efficiently used to prevent or treat cancer.

According to another aspect of the present disclosure, a method of screening a substance which inhibits the expression of CCND3 gene or PAK2 gene may be able to screen a candidate substance for preventing or treating cancer.

BRIEF DESCRIPTION OF DRAWINGS

FIGS. 6A-6C show binding of miR-4779 (SEQ ID NO: 3) to the 3' UTR of target genes PAK2 and CCND3.

The Sequence Listing is submitted as an ASCII text file in the form of the file named Sequence_Listing.txt, which was created on Apr. 13, 2020, and is 1.6 kilobytes, which is incorporated by reference herein.

MODE OF DISCLOSURE

Hereinafter, the present disclosure will be described in detail with reference to Examples. However, these Examples are provided for illustrative purposes only, and the present disclosure is not limited thereto.

EXAMPLE 1

Screening of Tumor-Inhibiting miRNA and Radiation Sensitivity-Enhancing miRNA

1. Protocols
(1) Cell Culture

Two types of human colon cancer cell lines (i.e., HCT116 and HT-29) were respectively cultured at 37° C. in a humidified chamber supplied with 5% $CO_2$ in RPMI-1640 or DMEM, each supplemented with 10% fetal bovine serum (FBS), 100 U/ml penicillin, and 100 μg/ml streptomycin sulfate.

(2) Irradiation

For ionizing radiation (IR), gamma IR was irradiated by using a Gammacell 3000 Elan irradiator ([137Cs] γ-ray source; MDS Nordin, Canada).

(3) miRNA Library Transfection 0.6 μl of 20 μM miRNA concentrate was diluted with 10 μl of PBS to have a final concentration of 50 nM, and 0.4 μl of G-fectin (Genolution, Korea) was diluted with 10 μl of PBS. The two diluted solutions were added to each well of a 96-well plate, mixed well, and left for 5 minutes. HCT116 cells or HT-29 cells were diluted to have a concentration of $2 \times 10^3$ cell/80 μl medium, and then, 80 μl of the cells was dispensed to each well containing 532 miRNA/G-fectin composites, and mixed well. The cells were cultured at 37° C. according to the experimental conditions.

(4) Screening of Tumor-Inhibiting miRNA

HCT116 cells were transfected with miRNAs and then cultured for 72 hours, and a cell proliferation rate thereof was measured by the MTS analysis. Each sample was tested in triplicate for each experiment, and the experiment was repeated three times to select miRNAs that reduced the average cell proliferation rate to 50% or less.

(5) Screening of Radiation Sensitivity-Enhancing miRNA

HT-29 cells were transfected with 532 miRNAs, and two identical sample plates were prepared. 16 hours after transfection, each plate was irradiated with 0 Gy or 6 Gy. Then, the cells were culture for another 72 hours after the irradiation, and a cell proliferation rate thereof was measured by the MTS analysis. Each sample was tested in triplicate for each experiment, and the experiment was repeated three times to select miRNAs that reduced the average cell proliferation rate to 50% or less by treating the cells with miRNA in combination with irradiation.

(6) Analysis of Proliferation Rate

To measure the proliferation rate, the MTS assay was performed by using the CellTiter 96® AQueous One Solution Cell Proliferation Assay kit (Promega, USA).

In detail, 20 μl of MTS solution was added to each well (100 μl medium/well) of a 96-well plate, and the cells were cultured for another 2 to 4 hours. Then, absorbance thereof was measured at A490 nm, and the proliferation rate was indicated in % with respect to miR-NC, which is a negative control for each cell.

(7) Results of Screening

As tumor-inhibiting miRNAs that reduced the proliferation rate of the HCT116 cells to 50% or less, 30 types of miRNAs were discovered. In addition, as radiation sensitivity-enhancing miRNAs that reduced the proliferation rate of the HT-29 cells to 50% or less by treating the cells with miRNA in combination with irradiation, 29 types of miRNAs were discovered. Consequently, miR-4779 (5'-uag-gagggaa uaguaaaagc ag-3', SEQ ID NO: 3) commonly included in both 30 types of the tumor-inhibiting miRNAs and 29 types of the radiation sensitivity-enhancing miRNAs was finally screened.

EXAMPLE 2

Effects of miR-4779 on Cell Proliferation, Apoptosis, Cell Viability, and Adhesion-Dependent Cell Growth 1. Confirmation of Cell Proliferation Rate due to Overexpression of miR-4779 in HCT116 Cells As described in Example 1.1(3), the HCT116 cells were transfected with miR-NC and miR-4779. 72 hours after incubation, cell proliferation rates were measured according to the MTS analysis.

Figure 1A:
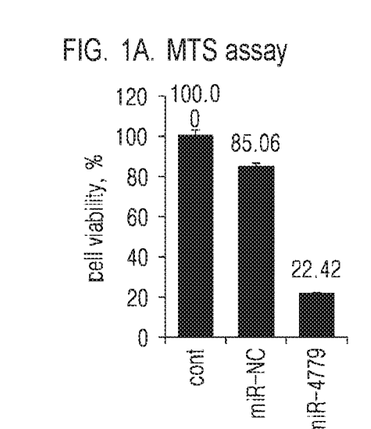
FIGS. 1A-1D show cell proliferation (FIG. 1A), cell morphology (FIG. 1B), cell cycle (FIG. 1C), and apoptosis (FIG. 1D), when miR-4779 is overexpressed in HCT116 cells.
Figure 1B:
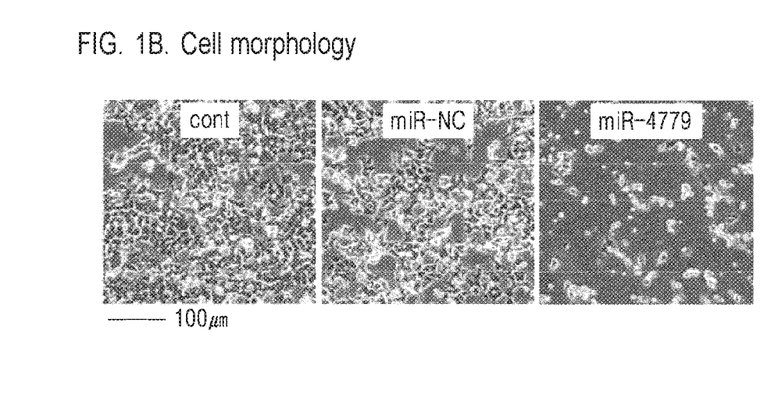

As shown in FIGS. 1A and 1B, when miR-4779 was overexpressed in the HCT116 cell line and the cell proliferation was confirmed by the MTS analysis and microscopic observation, it was confirmed that the cell proliferation of miR-4779-treated cells was significantly reduced as compared to an untreated control group (cont.) and a non-targeting negative control miRNA (miR-NC).

2. Confirmation of Effects of Overexpression of miR-4779 in HCT116 Cells on Cell Cycle The cell cycle analysis was confirmed to confirm whether the cell proliferation inhibition of Example 2.1 was due to cell cycle delay.

For the cell cycle analysis experiments, 500 μl of OPTI-MEM (Invitrogene, USA) was added to a 6-well plate first. 7.5 μl of 20 μM miRNA concentrate (miR-NC or miR-4779) and 5 μl of lipopectamine RNAiMAX (Invitrogene) were added to the plate to have a final concentration of 50 nM, mixed well, and left for 5 minutes. The HCT116 cells were diluted to have a concentration of $5 \times 10^5$ cells/2.5 ml medium, and then, 2.5 ml of the cells was dispensed to each well containing miRNA/G-fectin composites, and mixed well. The cells were then additionally cultured at 37° C. The resulting cells were transfected with miR-NC and miR-4779. After incubation for 48 hours, the cells were collected. Each cell washed with cold PBS buffer solution was suspended again in 1 ml of PBS, and the number of the cells was counted. $2 \times 10^6$ of the cells were each slowly added to a tube containing 4 ml of cold 70% ethanol, mixed well, and left overnight at 4° C. to fix the cells. The cells fixed with 70% ethanol were centrifuged (at 2,000×g for 10 minutes) to remove ethanol therefrom, 5 ml of PBS was added thereto, and the resulting mixture was left at room temperature for 10 minutes. A centrifugation process was performed again thereon, the cells were suspended in 100 μl of PBS and 100 μl 2× propidium iodide (PI) staining solution (i.e., PBS solution containing 50 μg/ml PI, 2 μg/ml DNase-free RNase A, and 0.2% NP-40) was added thereto to block light, and the reaction was allowed at room temperature for 30 minutes. Afterwards, the cell cycle was measured by the FACS analysis using BD FACSCanto II flow cytometer (BD Biosciences, USA).

Figure 1C:
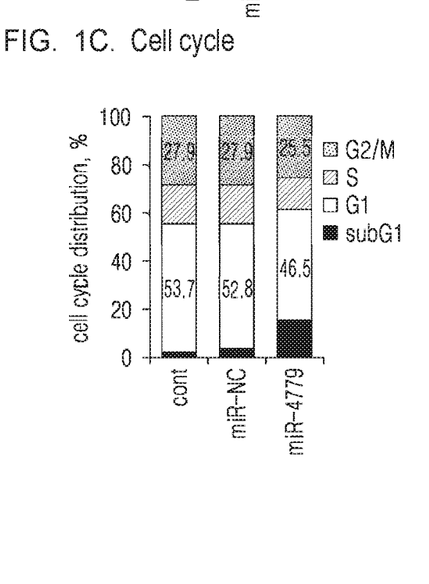

Consequently, as shown in FIG. 1C, it was confirmed that the overexpression of miR-4779 increased the number of the HCT116 cells at subG1 and G1 phases, and that the number of the HCT116 cells at subG1 phase was significantly increased.

3. Confirmation of Effects of Overexpression of miR-4779 in HCT116 Cells on Apoptosis To confirm again whether the inhibitory effects of miR-4779 on the cell proliferation shown in Examples 2.1 and 2.2, an apoptosis assay was performed by using the Annexin V-FITC Apoptosis Detection Kit (BioVision, USA) through Annexin V-FITC/PI double staining.

For the apoptosis analysis, as described in Example 2.2, the HCT116 cells were transfected with miR-NC or miR-4779 in a 6-well plate. 48 hours after the transfection, the cells were collected. Each cell washed with cold PBS buffer solution was suspended again in a reaction buffer solution (10 mM HEPES, pH 7.4, 140 mM NaCl, 25 mM $CaCl_2$), and the number of the cells was counted. 5 μl of PI solution and 5 μl of Annexin V-FITC solution were added to each of $5 \times 10^5$ cells/100 μl to block light, and the reaction was allowed at room temperature for 10 minutes. Afterwards, an FACS analysis was performed. Here, Annexin V-FITC positive cells (at the initial stage of apoptosis) and PI positive cells (at the end stage of apoptosis) were combined and indicated in % with respect to the total cells.

Figure 1D:
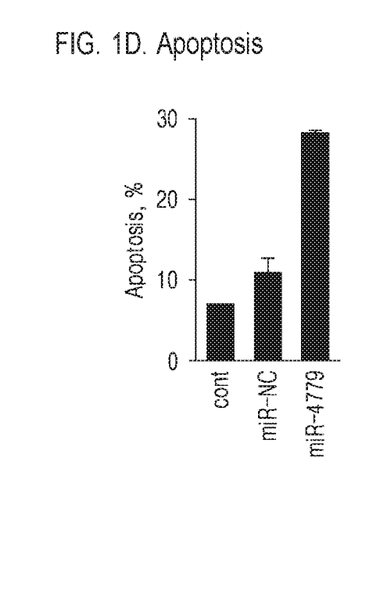

Consequently, as shown in FIG. 1D, it was confirmed that the apoptosis of the miR-4779-treated cells was increased 2.5 times higher than the apoptosis of the miR-NC-treated cells.

4. Confirmation of Cell Viability Due to Overexpression of miR-4779 in HCT116 Cells To measure the cell viability due to overexpression of miR-4779, the colony forming assay was performed.

For the colony forming assay, as described in Example 2.2, the HCT116 cells were transfected with miR-NC or miR-4779 in a 6-well plate. 24 hours after the transfection, the cells were collected respectively, and the number of the cells was counted. 200 cells were inoculated into a new 6-well plate, and additionally cultured for 7 days. The formed colonies were stained with 0.4% crystal violet at room temperature for 5 minutes, and the extra staining solution was washed with running water and dried. Images obtained therefrom were scanned, and the number of the stained colonies was counted. Each experiment was performed in triplicate.

Figure 2A:
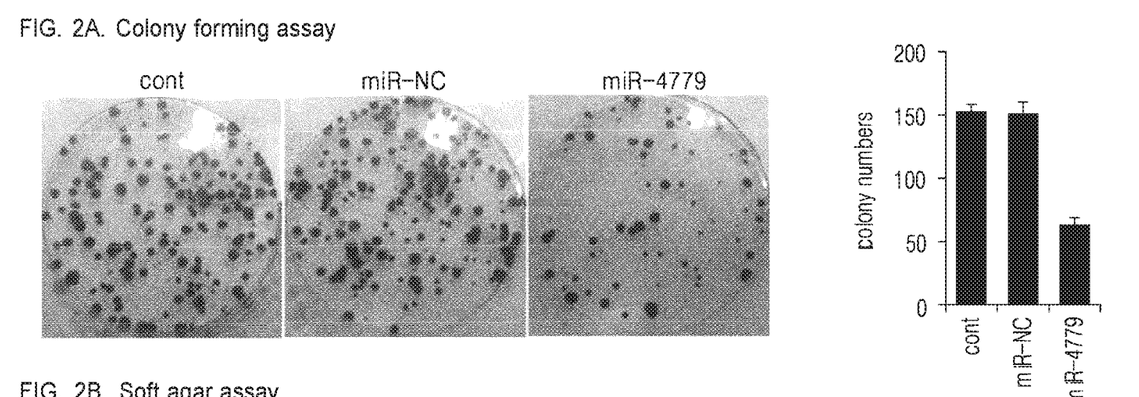
FIGS. 2A and 2B show cell viability (FIG. 2A) and adhesion-dependent cell proliferation (FIG. 2B), when miR-4779 is overexpressed in HCT116 cells.

Consequently, as shown in FIG. 2A, it was confirmed that the number of the colonies formed in the cells overexpressing miR-4779 was reduced by three times or more as compared with the control group and the miR-NC-treated cells.

5. Analysis of Adhesion-Dependent Cell Proliferation Due to Overexpression of miR-4779

To measure adhesion-dependent cell proliferation due to overexpression of miR-4779, a soft agar assay was performed.

For the soft agar assay, as described in Example 2.1, 6 the HCT116 cells were transfected with miR-NC or miR-4779 in a 6-well plate. 24 hours after the transfection, the cells were collected respectively, and the number of the cells was counted. 2,000 cells were diluted with a medium containing 1 ml of 0.3% agar (2,000 cells/1 ml of 0.3% agar-containing medium), and then, 1 ml of the cells was dispensed to a 6-well plate coated with 0.8% agar. The plate was left in a clean bench for 30 minutes to solidify the agar, and the cells were cultured for another 14 days. 0.5 ml of INT (iodonitrotetrazolium violet, 0.5 mg/ml in PBS) solution was added to each well, and the reaction was allowed overnight to stain colonies. Images obtained the plate containing the stained colonies were scanned, and the number of the stained colonies was counted.

Figure 2B:
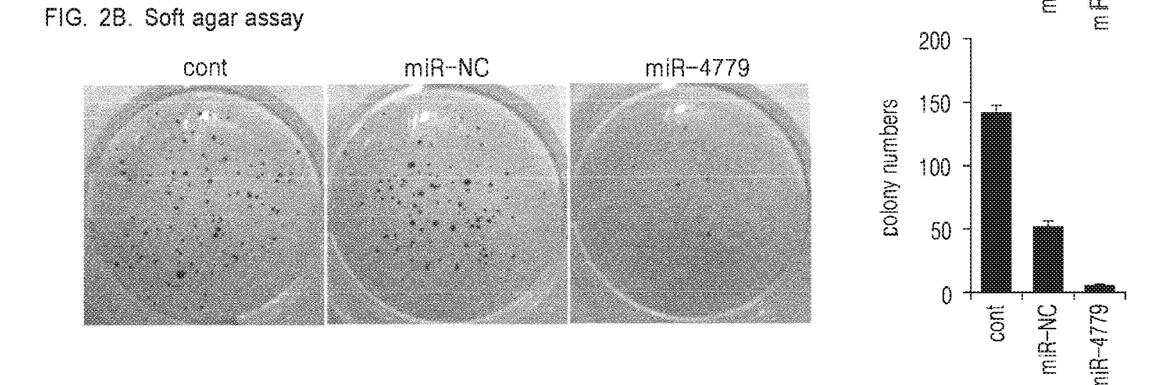

Consequently, as shown in FIG. 2B, it was confirmed that the number of colonies formed in the adhesion-dependent cells overexpressing miR-4779 was significantly decreased as compared to the miR-NC-treated cells.

EXAMPLE 3

Effects of Overexpression of miR-4779 on Radiation Sensitivity Enhancement

1. Analysis of Cell Proliferation by Combined Treatment of miR-4779 and Irradiation As described in Example 1.1.(3), the HT-29 cells were transfected with miR-NC and miR-4779. 16 hours after the transfection, the cells were irradiated (0 Gy and 6 Gy), and cultured for 72 hours. Then, a cell proliferation rate thereof was measured by the MTS analysis.

Figure 3A:
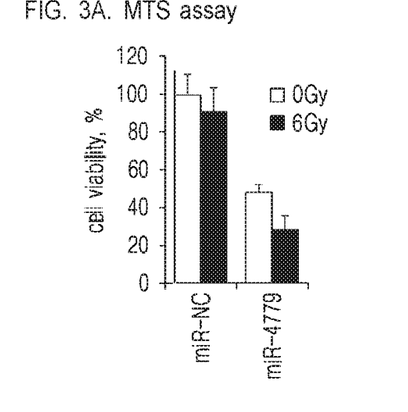
FIGS. 3A-3C show effects of combined radiation treatment on cell proliferation (FIG. 3A), cell cycle (FIG. 3C), and cell morphology (FIG. 3B), when miR-4779 is overexpressed in HT-29 cells.
Figure 3B:
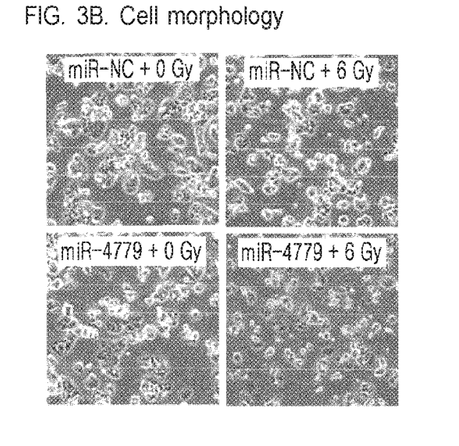

Consequently, as shown in FIG. 3A, the cell proliferation upon irradiation was significantly reduced in the cells overexpressing miR-4779 as compared with the miR-NC-treated cells. That is, it was confirmed that the overexpression of miR-4779 increased the sensitivity to radiation in the HT-29 cells which is radiation-resistant cancer cell line. In addition, as shown in FIG. 3B, the morphology of the cells overexpressing miR-4779 changed more remarkably when irradiated, indicating increased sensitivity to radiation.

2. Analysis of Effects of Combined Treatment of miR-4779 and Irradiation on Cell Cycle and Apoptosis To whether the cell proliferation inhibition of Example 3.1 was due to cell cycle delay, as described in Example 2.2, the HT-29 cells overexpressed miR-4779 and irradiated (0 Gy and 6 Gy). 48 after the irradiation, a cell cycle analysis was performed.

Figure 3C:
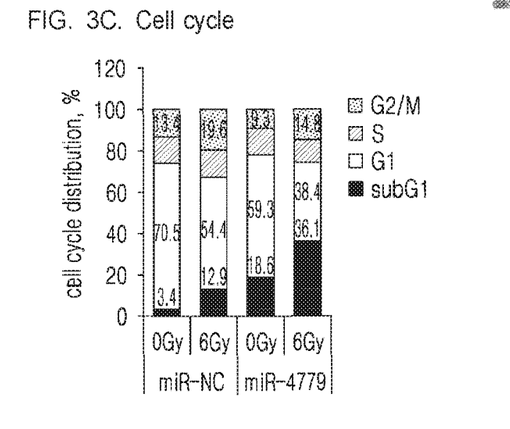

FIG. 3C shows the results of the cell cycle analysis performed by overexpressing miR-4779 in the HT-29 cells and irradiating the cells. As shown in FIG. 3C, it was confirmed that single treatment using irradiation caused cell cycle delay in G2/M phase and simultaneously increased the number of the cells at subG1 phase. In addition, it was confirmed that single treatment using miR-4779 decreased the number of the cells at G2/M phase and increased the number of the cells at subG1 phase. That is, the combination of miR-4779 overexpression and irradiation treatment was found to exhibit synergistic effects in terms of the increased number of the cells at subG1 phase (i.e., apoptosis) by single treatment using irradiation or single treatment using miR-4779. In addition, it was also found that the cell cycle delay at G2/M phase by the irradiation treatment was also maintained in the cells overexpressing miR-4779.

3. Analysis of Combined Treatment of miR-4779 Overexpression and Irradiation on Cell Viability and Irradiated Adhesion-Dependent Cell Proliferation To confirm cell viability upon the combined treatment of miR-4779 overexpression and irradiation, the colony forming assay was performed.

In detail, as described in Example 2.1, the HCT116 cells were transfected with miR-NC or miR-4779 in a 6-well plate. 16 hours after the transfection, the cells were irradiated (0 Gy and 2 Gy), collected, and subjected to the colony forming assay and the soft agar assay described in Examples 2.4 and 2.5, respectively.

Figure 4A:
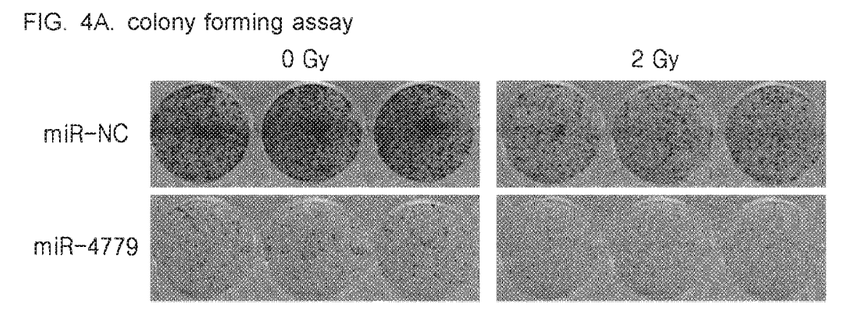
FIGS. 4A and 4B show the results of radiation sensitivity based on cell viability (FIG. 4A) and adhesion-dependent cell proliferation (FIG. 4B), when miR-4779 is overexpressed in HT-29 cells.
Figure 4B:
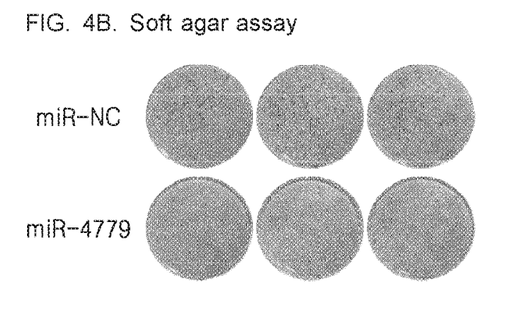

Consequently, as shown in FIG. 4A, it was confirmed that the radiation sensitivity was increased by overexpression of miR-4779 based on the significantly reduced number of the colonies by irradiation in the cells overexpressing miR-4779 as compared to the miR-NC-treated cells. In addition, similar to the results of Example 2.5 and as shown in FIG. 4B, when the HT-29 cells overexpressed miR-4779, the adhesion-dependent cell growth thereof was completely eliminated without irradiation.

EXAMPLE 4

Conformation of Target Gene of miR-4779

1. Prediction of Target Gene of miR-4779

To discover target genes related to the tumor-inhibiting functions of miR-4779, cyclin D3 (CCND3) and p21-activated kinase 2 (PAK2) were selected from as candidate target genes related to cell growth or apoptosis through the prediction database for target genes of miRNA (miRDB and Targetscan).

2. Decrease in mRNA Expression of CCND3 and PAK2 Genes Due to Overexpression of miR-4779

To confirm the mRNA expression level of CCND3 and PAK2 genes, which were selected from as candidate target genes of miR-4779, a qRT-PCR analysis was performed.

In detail, the HCT116 cells were transfected with 50 nM miR-NC or miR-4779. 20 hours after the transfection, each cell was collected, and total RNAs were extracted therefrom by using the RNeasy mini kit (Qiagen, USA). 10 μl of cDNA was synthesize by using 1 μg RNA as a template and the PrimeScript RT Master Mix (Takara, Japan). The cDNAs were subsequently diluted 5-fold for the qRT-PCR analysis, and the qRT-PCR was performed by using the 2× Power SYBR Green PCR Master Mix (Applied Biosystem, USA) and validated q-RT primer (Bioneer, Korea) for hCCND3, hPAK2, and hHPRT1.

Figure 5A:
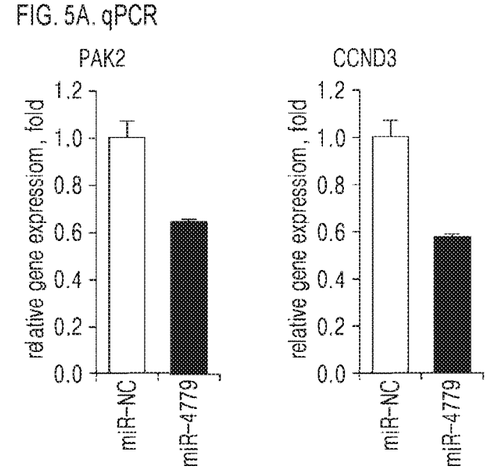
FIGS. 5A and 5B show the expression of mRNAs and proteins of CCND3 and PAK2 which are predicted target genes upon the overexpression of miR-4779 in HCT116 cells, wherein the expression of the mRNAs (FIG. 5A) and the proteins (FIG. 5B) of both genes is reduced by miR-4779.

Consequently, as shown in FIG. 5A, it was confirmed that the mRNA expression of the CCND3 and PAK2 genes was down-regulated by miR-4779.

3. Decrease in Protein Expression of CCND3 and PAK2 Genes Due to Overexpression of miR-4779

To confirm the protein expression quantity of CCND3 and PAK2 genes, which were selected from as candidate target genes of miR-4779, a western blot analysis was performed.

First, the HCT116 cells were transfected with 50 nM miR-NC or miR-4779. 48 hours after the transfection, each cell was washed with cold PBS buffer solution. Here, total proteins were extracted with a buffer solution for cell extraction (20 mM Tri-HCl, pH 6.8, 2% SDS, 2 mM EDTA, 1 mM $Na_3VO_4$, 1 mM DTT, 20% glycerol, and 0.5 mM PMSF), and ultrasonicated using an ultrasonicator until the total protein extract was no longer sticky. The quantity of the total proteins of the cell extract was measured by using the BCA Protein Assay Kit (Pierce, USA), wherein bovine serum albumin (BSA) was used as a reference protein. The quantified total proteins were added to a sample buffer solution for SDS-PAGE, and the mixed solution was boiled at 95° C. for 5 minutes before use. The same amount of the proteins was electrophoresed on the 12% SDS-PAGE, and then, the western blot analysis was performed by using anti-CCND3 (cell signaling, USA), anti-PAK2 (cell signaling), and anti-β-actin (sigma, USA).

Figure 5B:
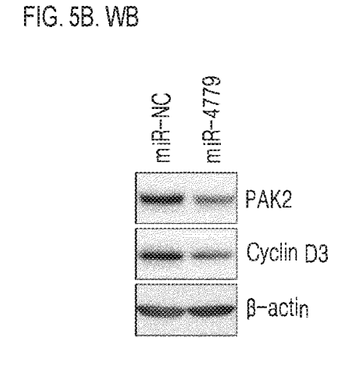

As shown in FIG. 5B, the western blot analysis results showed that both proteins were significantly reduced in the miR-4779-treated sample as compared to the miR-NC negative control. Accordingly, it was confirmed that CCND3 and PAK2 were down-regulated by miR-4779 as target genes of miR-4779.

4. Confirmation of Binding of miR-4779 to 3'-UTR of CCND3 or PAK2

Whether miR-4779 directly binds CCND3 and PAK2 which are predicted to be target genes was confirmed by measuring the luciferase activity of several 3'-UTR DNA constructs of the two genes as described below.

Figure 6A:
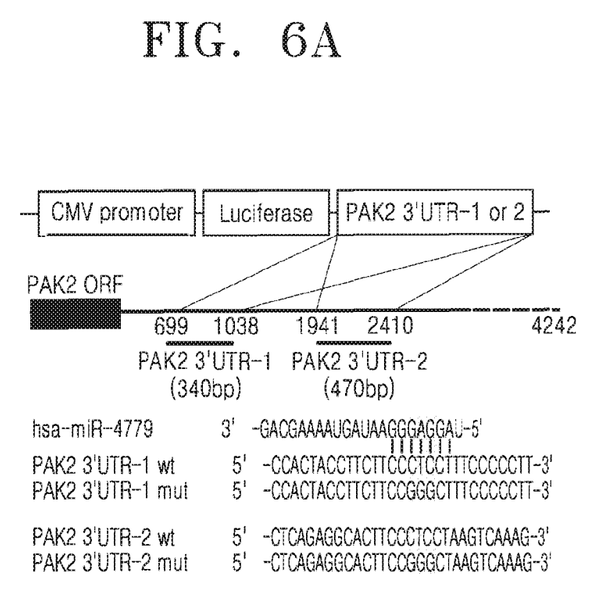
FIG. 6A shows a sequence alignment of miR-4779 (SEQ ID NO: 3) with PAK2 3' UTR-1 wt (SEQ ID NO: 4), PAK2 3' UTR-1 mut (SEQ ID NO: 5), PAK2 3' UTR-2 wt (SEQ ID NO: 6), and PAK2 3' UTR-2 mut (SEQ ID NO: 7).
Figure 6B:
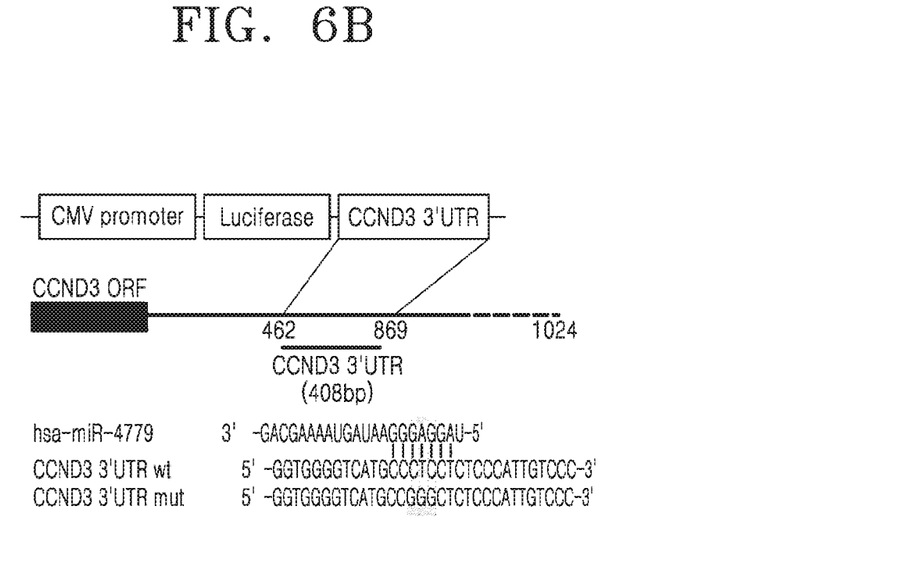
FIG. 6B shows a sequence alignment of miR-4779 (SEQ ID NO: 3) with CCND3 3' UTR wt (SEQ ID NO: 8) and CCND3 3' UTR mut (SEQ ID NO: 9).

First, as shown in FIGS. 6A and 6B, the position of a base sequence (-CCCTCCT-) which is complementary to a seed sequence (-AGGAGGG-) of miR-4779 on the 3'-UTR of the two genes was identified by using a TargetScan analysis program. As a result of the analysis on the 3'-UTR of the PAK2, two miR-4779-binding base sequences (894-900, 2106-2112) were found, and as a result of the analysis on the 3'-UTR of the CCND3, there was one miR-4779-binding base sequence (795-800) was found.

The 3'UTR DNA constructs (PAK2 3'UTR-1, PAK2 3'UTR-2, CCND3 3'UTR) of the two genes including the three selected from miR-4779-binding base sequences were amplified by PCR using the HCT116 cDNA as a template, and then, cloned into the back of the luciferase gene of pGL3 vector (Promega, USA), thereby preparing three types of plasmid DNAs. The miR-4779-binding base sequence (-CCCTCCT-) of the three types of the plasmid DNAs (wild-type (wt)) was substituted with (-CCGGGCT-) by using the QuickChange II XL Site-Directed Mutagenesis kit (Agilent Technologies, USA), and three types of mutant (mut) plasmid DNAs that did not bind miR-4779 were also prepared.

$5×10^4$ HCT116 cells were inoculated into a 24-well plate ($5×10^4$ cells/well), and left for 20 hours. One of six types of the prepared pGL3-Luc-3'UTR reporter plasmid DNAs (200 ng) and renilla luciferase reporter plasmid DNAs (10 ng, pRL-CMV, promega) was transfected with 10 nM miR-NC or 10 nM miR-4779 by using lipopectamin 2000 (Invitrogen). 48 after the transfection, the luciferase activity was measured by using the Dual-Luciferase Reporter Assay System (Promega). Then, the luciferase activity of each of the six types of the pGL3-Luc-3'UTR reporter plasmid DNAs was measured.

Figure 6C:
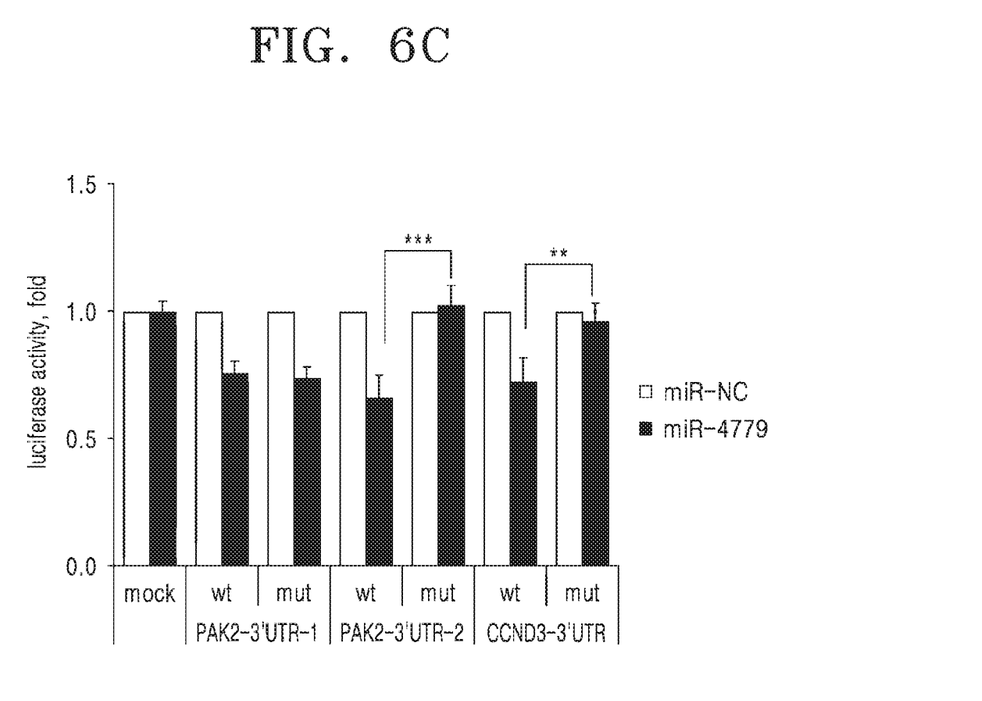

Consequently, as shown in FIG. 6C, in the case of a control (mock) not including the 3'-UTR DNA construct, the luciferase activity was not changed by miR-4779 as compared to the miR-NC-treated cells. In the case of the wild type of the PAK2 3'UTR-1, the luciferase activity was decreased by miR-4779, but such decreased luciferase activity by miR-4779 was also observed in the case of the mutant type. Accordingly, miR-4779 was not considered to specifically and directly bind the PAK2 3'UTR-1. In the case of the wild type of the PAK2 3'UTR-2, the luciferase activity was decreased by miR-4779, and there was no change in the luciferase activity by miR04779 in the mutant type. Therefore, it was confirmed that miR-4779 specifically and directly binds the PAK2 3'UTR-2. In the case of the wild type of the CCND3 3'UTR, the luciferase activity was decreased by miR-4779, and there was no change in the luciferase activity by miR04779 in the mutant type. Therefore, it was confirmed that miR-4779 specifically and directly binds the CCND3 3'UTR.

In conclusion, it was confirmed that PAK2 was a direct target gene of miR-4779 and that miR-4779 inhibited the expression of PAK2 by binding to the PAK2 3'UTR-2. In addition, it was also confirmed that CCND3 was a direct target gene of miR-4779 and that miR-4779 inhibited the expression of PAK2 by binding to the CCND3 3'UTR.

EXAMPLE 5

Confirmation of Effects of Target Genes of miR-4779, CCND3 and PAK2, on Expression Inhibition 1. Decrease in Cell Proliferation by Expression Inhibition of CCND3 or PAK2

To identify whether the inhibition of cell proliferation by overexpression of miR-4779 was due to the expression inhibition of CCND3 or PAK2, which is identified as a direct target gene of miR-4779, the HCT116 cells were transfected with each si-RNA (si-NC, si-CCND3, and si-PAK2), so as to inhibit the expression of each protein. Then, the cell proliferation rates were confirmed by microscopic observation and the MTS analysis.

Figure 7A:
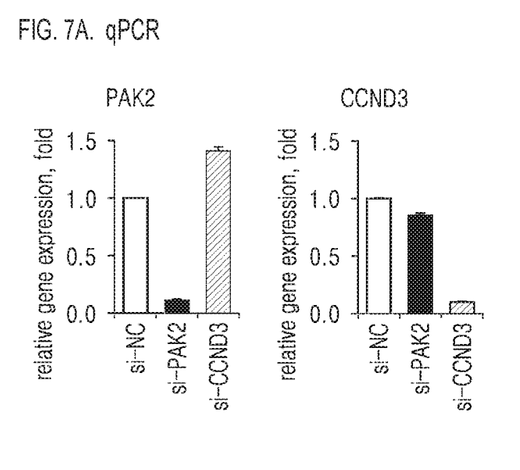
FIGS. 7A-7C show cell proliferation rates upon inhibition of the expression of CCND3 and PAK2, which are target genes of miR-4779.
Figure 7B:
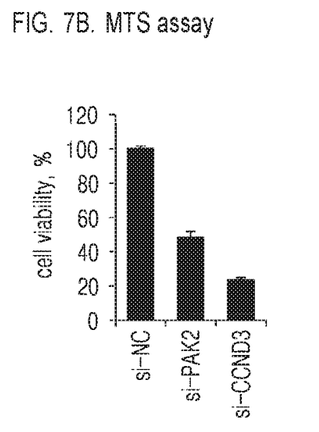
Figure 7C:
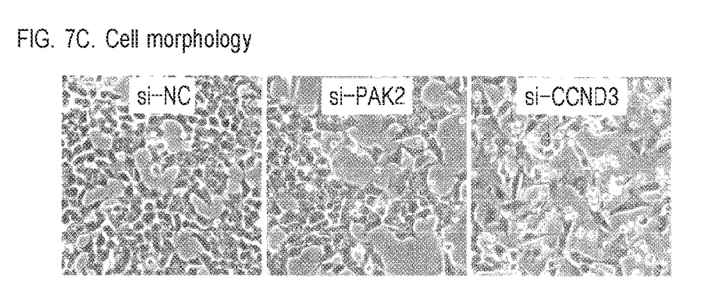

First, the HCT116 cells were transfected with si-CCND3 or si-PAK2. Then, as shown in FIG. 7A, the quantity of mRNAs of the PAK2 and the CCND3 genes was confirmed by qPCR, and accordingly, it was confirmed that the quantity of mRNAs of the genes corresponding to each si-RNA was remarkably decreased. Afterwards, as shown in FIG. 7B, the si-PAK2-treated cells showed a decrease in the cell proliferation rate by 50% while the si-CCND3-treated cells showed a decrease in the cell proliferation by 70%, as compared to a negative control which is the si-NC-treated cells. In addition, referring to cell morphology shown in FIG. 7C, it was confirmed that the cell growth was inhibited by si-PAK2 and the apoptosis was promoted by si-CCND3. From the above results, it was confirmed that the decrease in the cell proliferation by the overexpression of miR-4779 was a result of inhibition of cell proliferation by inhibition of PAK2 expression and promotion of apoptosis by inhibition of CCND3 expression at once.

2. Effects on Inhibition of CCND3 or PAK2 Expression on Cell Cycle

As described in Example 2.2, the cell cycle of the HCT116 cells when the expression of CCND3 or PAK2 was inhibited was analyzed.

Figure 8A:
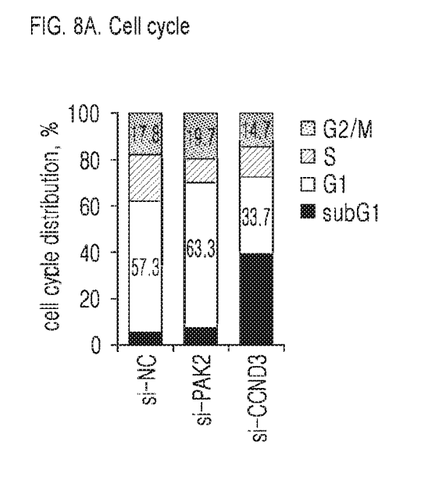
FIGS. 8A-8D show cell cycle (FIG. 8A), apoptosis (FIG. 8B), cell viability (FIG. 8C), and adhesion-dependent cell growth (FIG. 8D) upon inhibition of the expression of CCND3 and PAK2, which are target genes of miR-4779.

As shown in FIG. 8A, as compared to si-NC, the number of cells at subG1 phase was slightly increased by si-PAK2 while the number of cells at G1 phase was significantly increased. Accordingly, it was confirmed that the inhibition of the cell proliferation by si-PAK2 was due to the inhibition of the cell growth by the delay in the cell cycle mainly at G1 phase. Meanwhile, the number of cells at subG1 phase was increased by si-CCND3 as compared to si-NC, and accordingly, it was confirmed that the inhibition of the cell proliferation by si-CCND3 was due to the apoptosis.

3. Promotion of Apoptosis by Inhibition of Expression of CCND3 or PAK2

To more accurately confirm whether the increased apoptosis by miR-4779 was due to the inhibition of the expression of CCND3 rather than the inhibition of the expression of PAK2, the apoptosis analysis was performed as described in Example 2.3.

Figure 8B:
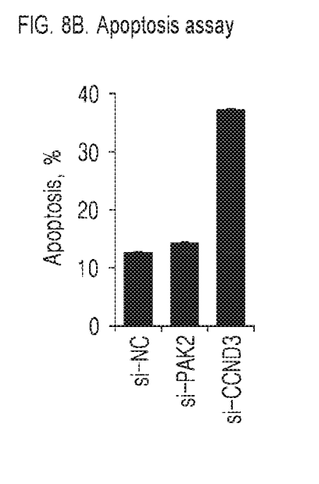

As shown in FIG. 8B, it was confirmed that the apoptosis was significantly increased by si-CCND3. Therefore, it was confirmed that the effects of the overexpression of miR-4779 on the apoptosis was due to the inhibition of the expression of CCND3.

4. Decrease in Cell Survival and Inhibition of Adhesion-Dependent Cell Growth by Inhibition of Expression of CCND3 or PAK2

As described in Examples 2.4 and 2.5, decrease in cell survival and inhibition of adhesion-dependent cell growth by the inhibition of the expression of CCND3 or PAK2 were confirmed by the colony forming analysis and the soft agar analysis.

Figure 8C:
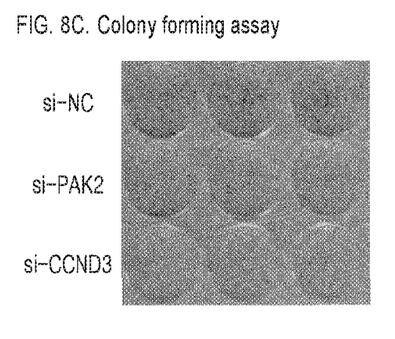
Figure 8D:
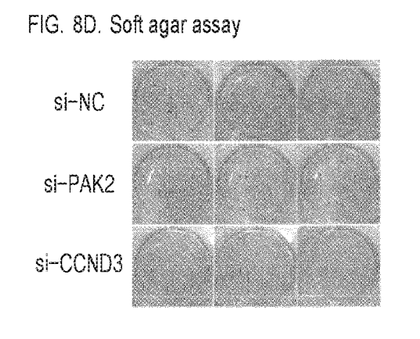

Consequently, as shown in FIGS. 8C and 8D, the number of colonies formed in the cells transfected with si-PAK2 or si-CCND3 was significantly reduced as compared to a control.

EXAMPLE 6

Effects of miR-4779 on Tumor Inhibition in HCT116 Xenograft Animal Model

Figure 9A:
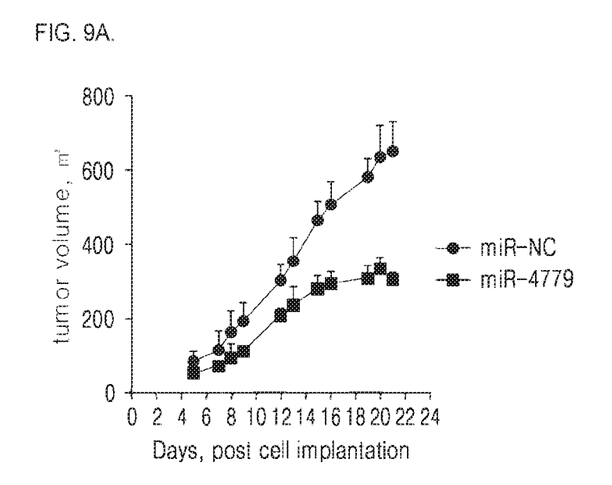
FIGS. 9A and 9B show effects of miR-4779 on the tumor inhibition in an HCT116-xenograft animal model.
Figure 9B:
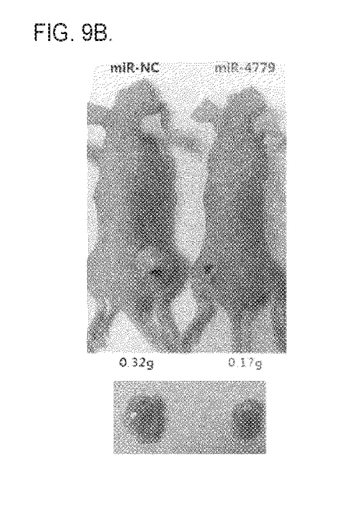

To confirm effects of miR-4779 on tumor inhibition in an animal model, a HCT116 xenograft animal model was prepared. First, $5 \times 10^6$ HCT116 cells were injected subcutaneously into the back of ten 5-week-old female immunodeficient mice (Balb/c-nude mouse) to generate tumors. When the tumors had the average volume of about 120 mm³, the mice were divided into two groups of five, and miR-NC or miR-4779 was injected in the in vivo-jetPEI/miRNA complex state in each group. The injection was made in each tumor two times at 3-day intervals. The volume of the tumors was measured twice a week (FIG. 9A). On the $22^{nd}$ day after the tumor transplantation, each mouse was photographed, and euthanized. Then, the tumors were extracted therefrom and weighed (FIG. 9B). FIGS. 9A and 9B show that the tumor volume was significantly reduced in the animal models injected with miR-4779, and accordingly, it was confirmed that miR-4779 had effects on in vivo tumor inhibition.

The invention claimed is:

1. A method of treating colon cancer, comprising administering to a subject a pharmaceutical composition comprising, as an active ingredient, a nucleic acid molecule comprising SEQ ID NO: 3.

2. The method of claim 1, wherein the nucleic acid molecule comprises consecutive nucleotides having a sequence complementarily binding to a 795-800 base sequence in mRNA 3' UTR of CCND3.

3. The method of claim 1, wherein the nucleic acid molecule comprises consecutive nucleotides having a sequence complimentarily binding to a 2016-2112 base sequence in mRNA 3' UTR of PAK2.

4. The method of claim 1, wherein the cancer is a condition that is resistant to radiation therapy.

5. The method of claim 1, wherein administering the pharmaceutical composition enhances radiation sensitivity of cancer cells.

6. The method of claim 1, wherein administering the substance inhibits the expression of both CCND3 gene and PAK2 gene.

7. A method of treating colon cancer, comprising administering to a subject a pharmaceutical composition comprising, as an active ingredient, an agent inducing generation of miRNA of SEQ ID NO: 3 and inhibiting the expression of cyclin D3 (CCND3) gene or p21-activated kinase 2 (PAK2) gene, wherein the agent is an miRNA expression vector.

8. The method of claim 7, wherein the miRNA comprises 7 to 100 consecutive nucleotides and comprises the nucleotide sequence of SEQ ID NO: 2.

* * * * *

SEQUENCE LISTING

```
<160> NUMBER OF SEQ ID NOS: 9

<210> SEQ ID NO 1
<211> LENGTH: 7
<212> TYPE: DNA
<213> ORGANISM: Homo sapiens

<400> SEQUENCE: 1 ccctcct                                                                    7

<210> SEQ ID NO 2
<211> LENGTH: 7
<212> TYPE: RNA
<213> ORGANISM: Homo sapiens

<400> SEQUENCE: 2 aggaggg                                                                    7

<210> SEQ ID NO 3
<211> LENGTH: 22
<212> TYPE: RNA
<213> ORGANISM: Homo sapiens

<400> SEQUENCE: 3
uaggagggaa uaguaaaagc ag                                                  22

<210> SEQ ID NO 4
<211> LENGTH: 29
<212> TYPE: DNA
```

```
<213> ORGANISM: Homo sapiens

<400> SEQUENCE: 4
ccactacctt cttccctcct ttcccctt                                              29

<210> SEQ ID NO 5
<211> LENGTH: 29
<212> TYPE: DNA
<213> ORGANISM: Homo sapiens

<400> SEQUENCE: 5
ccactacctt cttccgggct ttcccctt                                              29

<210> SEQ ID NO 6
<211> LENGTH: 29
<212> TYPE: DNA
<213> ORGANISM: Homo sapiens

<400> SEQUENCE: 6
ctcagaggca cttccctcct aagtcaaag                                             29

<210> SEQ ID NO 7
<211> LENGTH: 29
<212> TYPE: DNA
<213> ORGANISM: Homo sapiens

<400> SEQUENCE: 7
ctcagaggca cttccgggct aagtcaaag                                             29

<210> SEQ ID NO 8
<211> LENGTH: 32
<212> TYPE: DNA
<213> ORGANISM: Homo sapiens

<400> SEQUENCE: 8
ggtggggtca tgccctcctc tcccattgtc cc                                         32

<210> SEQ ID NO 9
<211> LENGTH: 32
<212> TYPE: DNA
<213> ORGANISM: Homo sapiens

<400> SEQUENCE: 9
ggtggggtca tgccgggctc tcccattgtc cc                                         32
```